US009292946B2

(12) United States Patent
Zou

(10) Patent No.: US 9,292,946 B2
(45) Date of Patent: Mar. 22, 2016

(54) X RAY COMPUTER TOMOGRAPHY APPARATUS AND IMAGE PROCESSING APPARATUS

(71) Applicants: KABUSHIKI KAISHA TOSHIBA, Tokyo (JP); TOSHIBA MEDICAL SYSTEMS CORPORATION, Otawara-Shi, Tochigi (JP)

(72) Inventor: Yu Zou, Naperville, IL (US)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 0 days.

(21) Appl. No.: 14/576,546

(22) Filed: Dec. 19, 2014

(65) Prior Publication Data

US 2015/0178958 A1      Jun. 25, 2015

Related U.S. Application Data

(63) Continuation-in-part of application No. 14/137,254, filed on Dec. 20, 2013.

(30) Foreign Application Priority Data

Nov. 20, 2014   (JP) .................................. 2014-235997

(51) Int. Cl.
*G06K 9/00*      (2006.01)
*A61B 6/00*      (2006.01)
(Continued)

(52) U.S. Cl.
CPC ............... *G06T 11/006* (2013.01); *A61B 6/032* (2013.01); *A61B 6/4233* (2013.01); *A61B 6/4241* (2013.01); *A61B 6/4266* (2013.01); *A61B 6/482* (2013.01); *A61B 6/5205* (2013.01); *G01T 1/00* (2013.01); *G06T 2211/408* (2013.01); *G06T 2211/424* (2013.01)

(58) Field of Classification Search
CPC ............. G06K 9/00; A61B 6/00; G06T 11/00
USPC ......... 382/128, 129, 130, 131, 132, 133, 134; 378/4, 8, 19, 21–27, 101, 901; 600/407, 410, 411, 425, 427
See application file for complete search history.

(56) References Cited

U.S. PATENT DOCUMENTS 7,022,073 B2 *   4/2006   Fan ...................... G06K 9/4609
                                                  600/437
7,471,767 B2 *  12/2008   Spahn .................... G03B 42/02
                                                  378/101
7,646,845 B2 *   1/2010   Lecomte ................. A61B 6/032
                                                  378/19

*Primary Examiner* — Abolfazl Tabatabai
(74) *Attorney, Agent, or Firm* — Yoshida & Associates, LLC

(57) ABSTRACT

An X-ray computer tomography apparatus includes at least one X-ray tube generating X-rays, first detector elements (energy integrating type) and second detector elements (photon counting type) detecting an intensity and spectrum of the X-rays transmitted through the object respectively, at least one data acquisition circuit acquiring first projection data and second projection data smaller in data amount than the first projection data detected by the first and second detector elements respectively, an arithmetic circuit computing a minimum value of a cost function based on the first and second projection data by executing an iterative reconstruction algorithm, and reconstruction circuit reconstructing an image of the object based on the first and second projection data, which correspond to the minimum value of the cost function.

11 Claims, 20 Drawing Sheets

(51) Int. Cl.
*G06T 11/00* (2006.01)
*A61B 6/03* (2006.01)
*G01T 1/00* (2006.01)

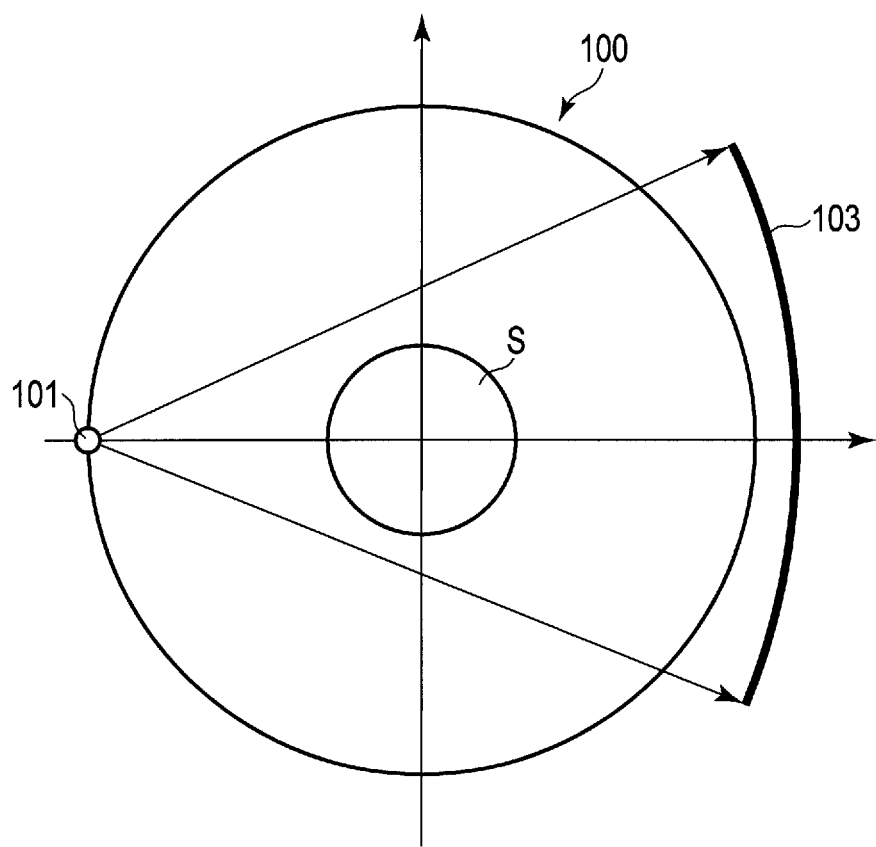
F I G. 2A

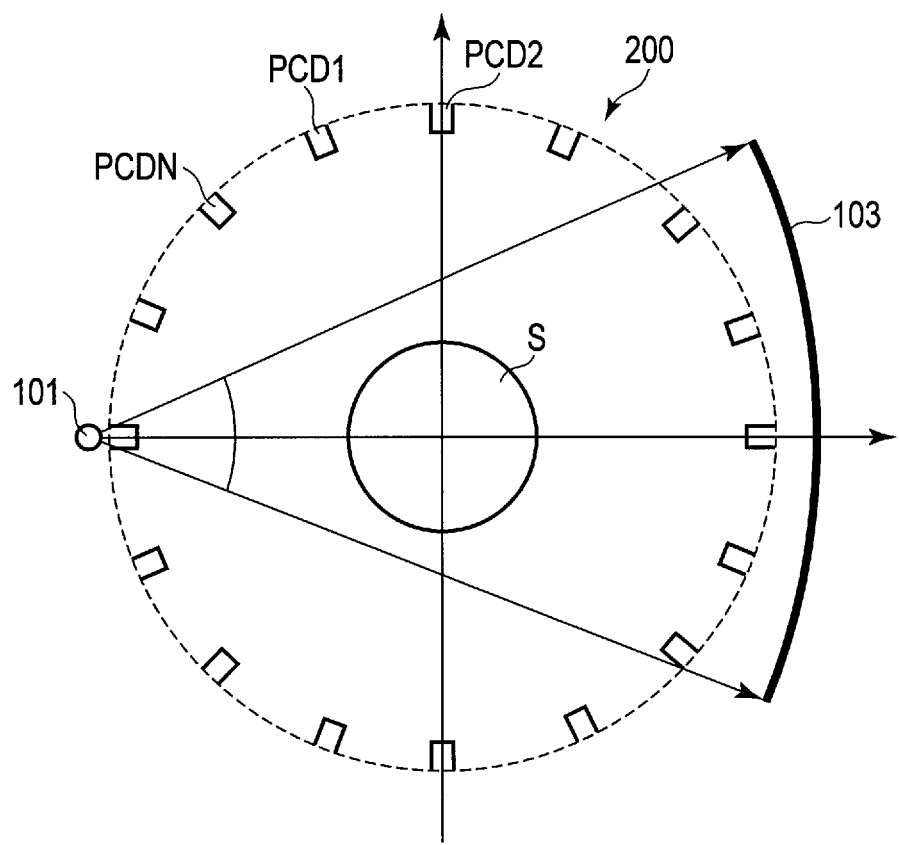
F I G. 2B

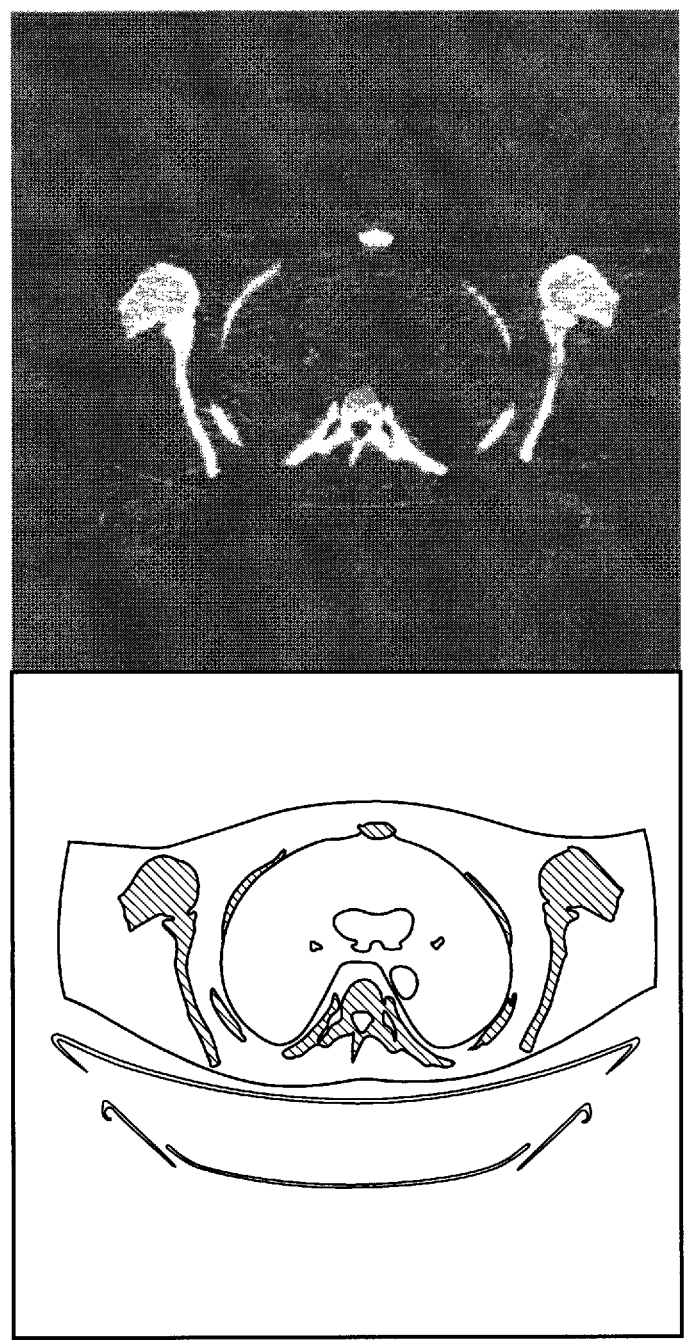
F I G. 4A

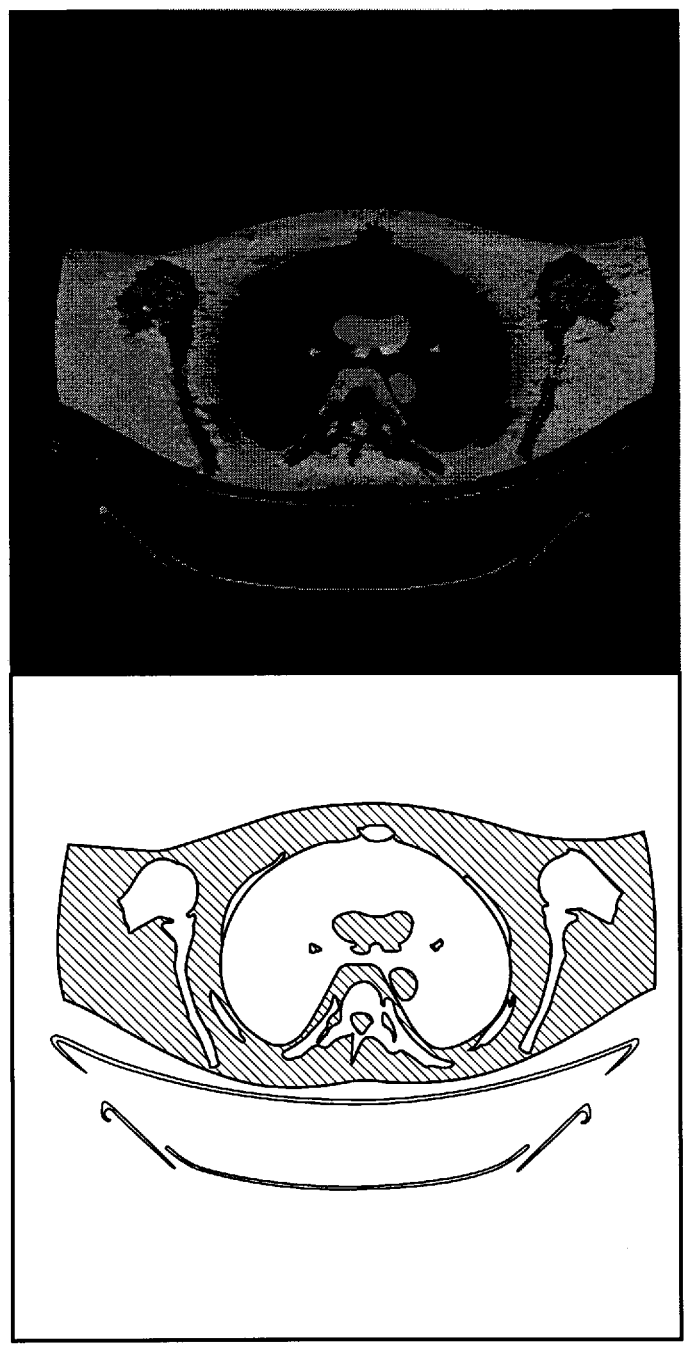
F I G. 4B

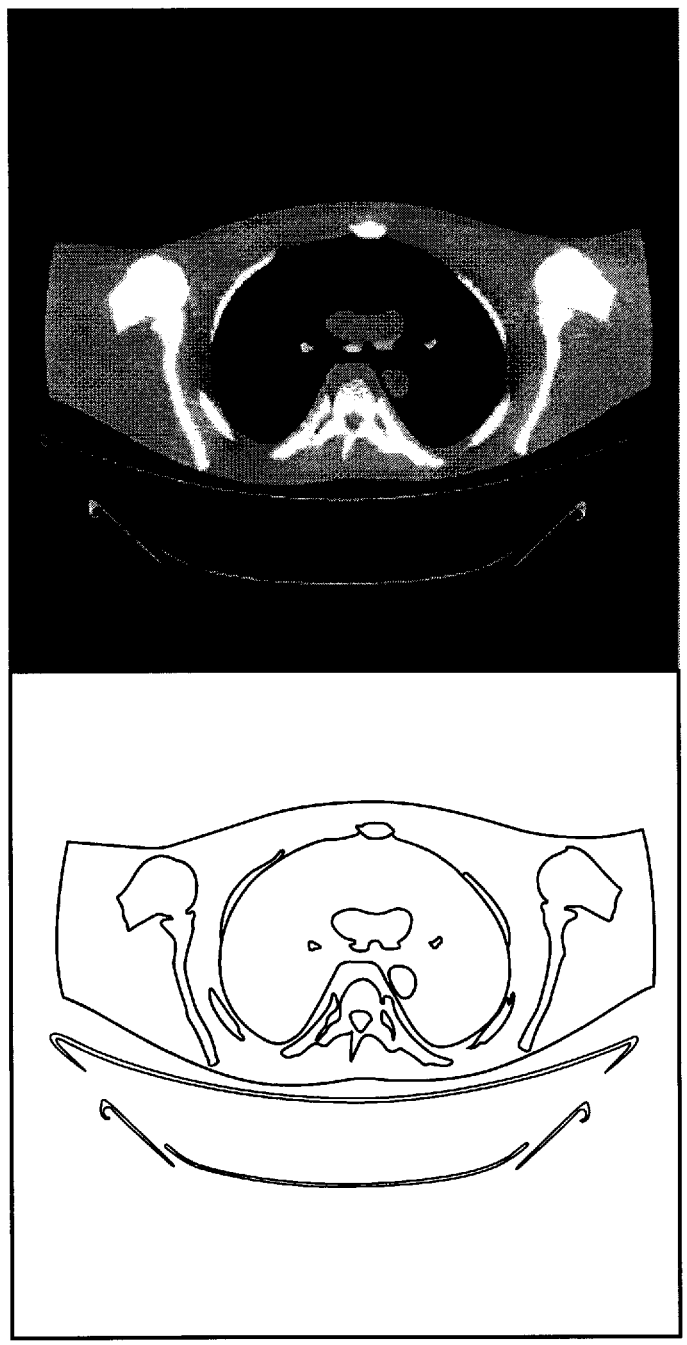
F I G. 4C

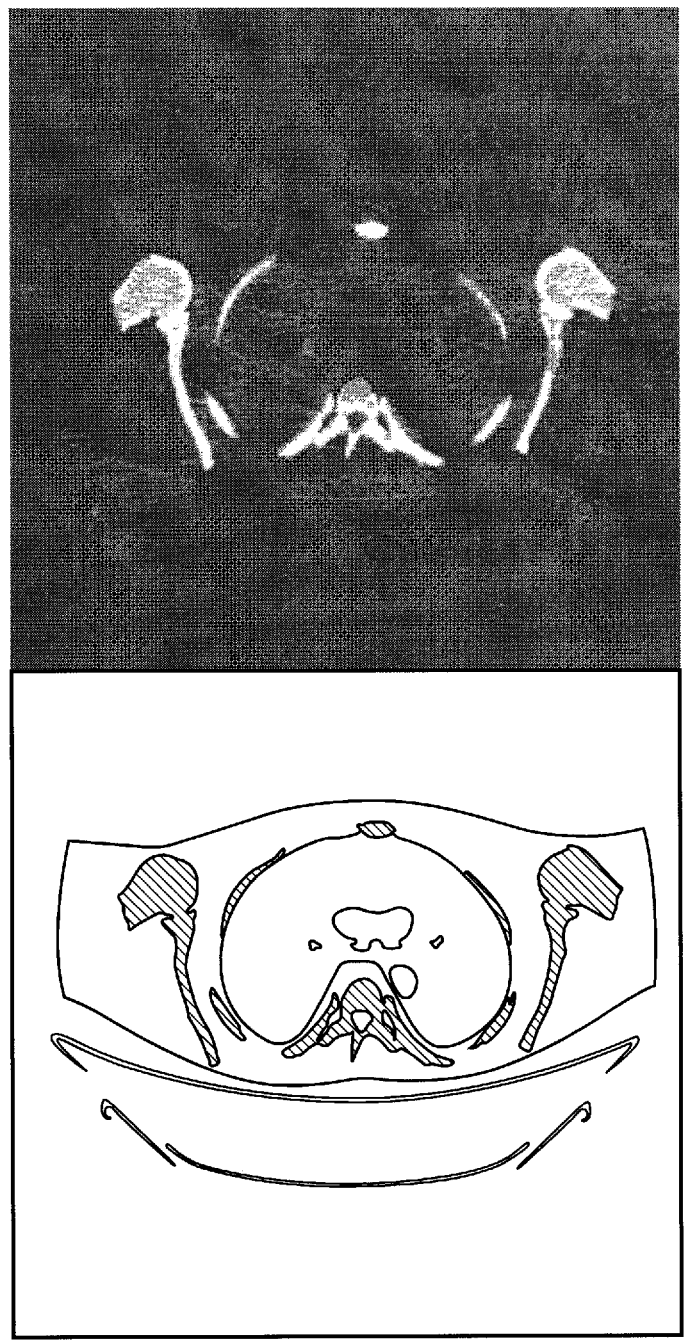
F I G. 5A

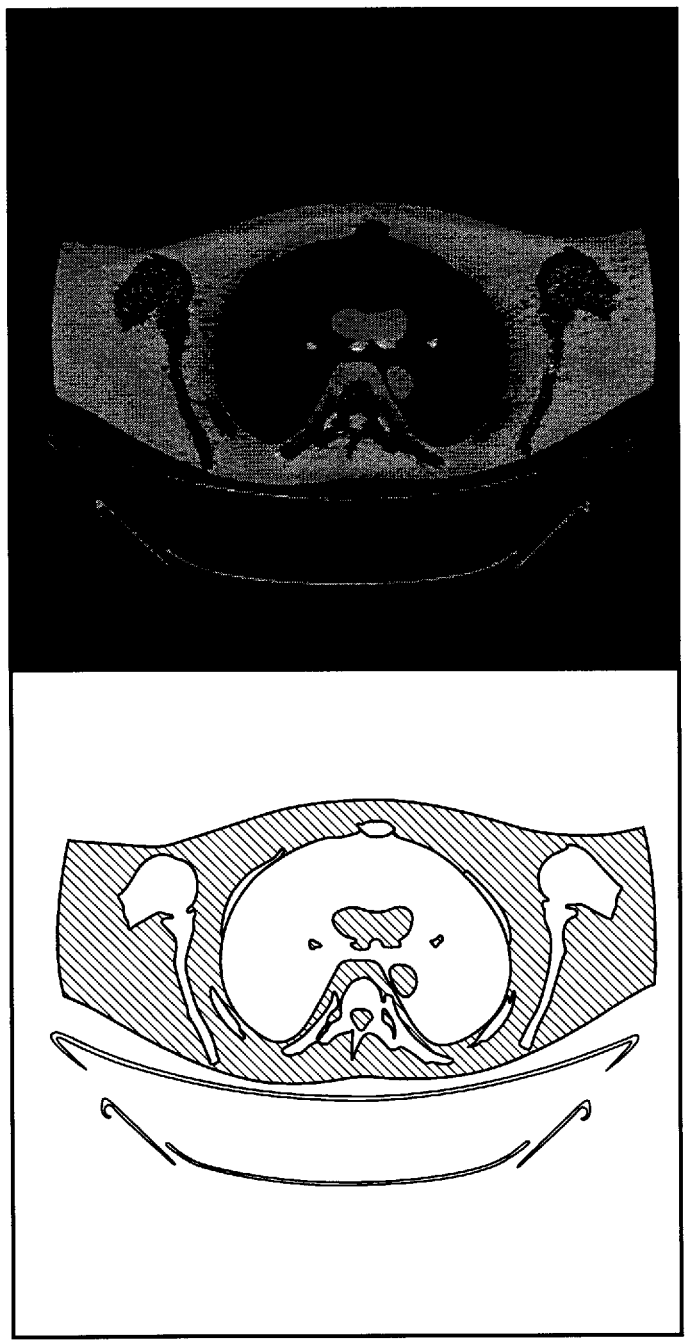
F I G. 5B

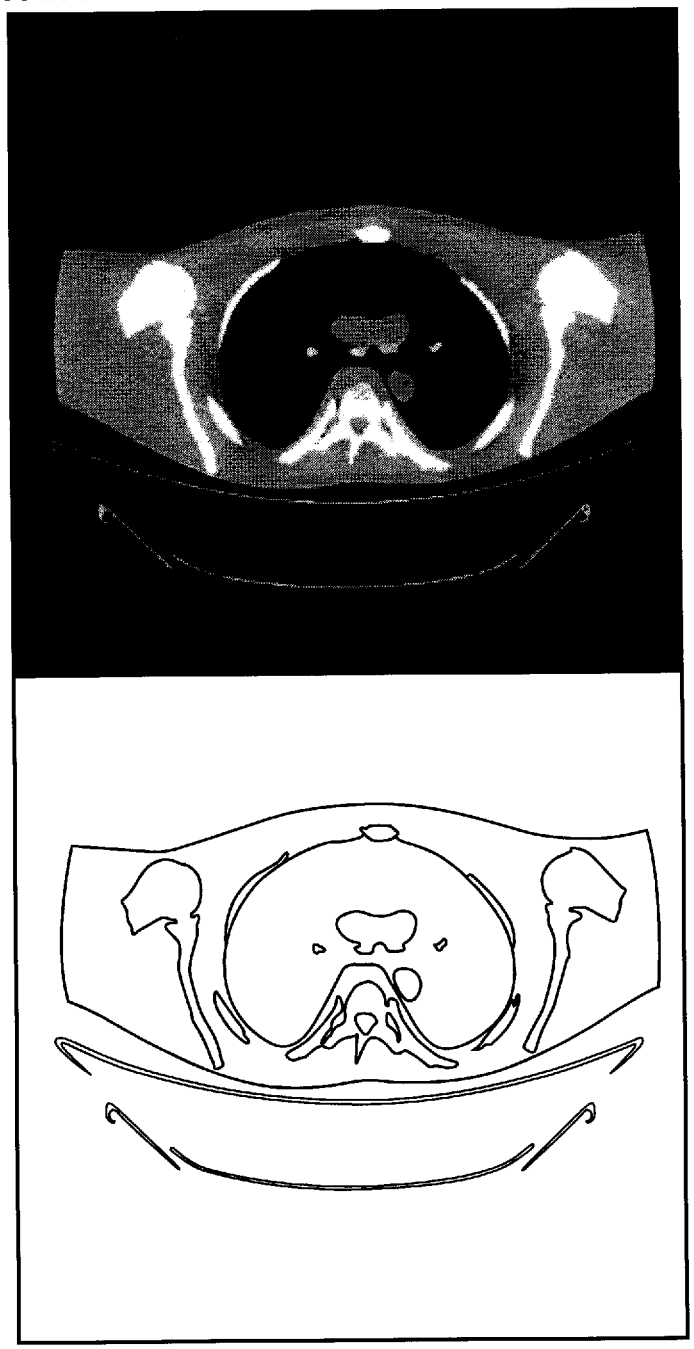
F I G. 5C

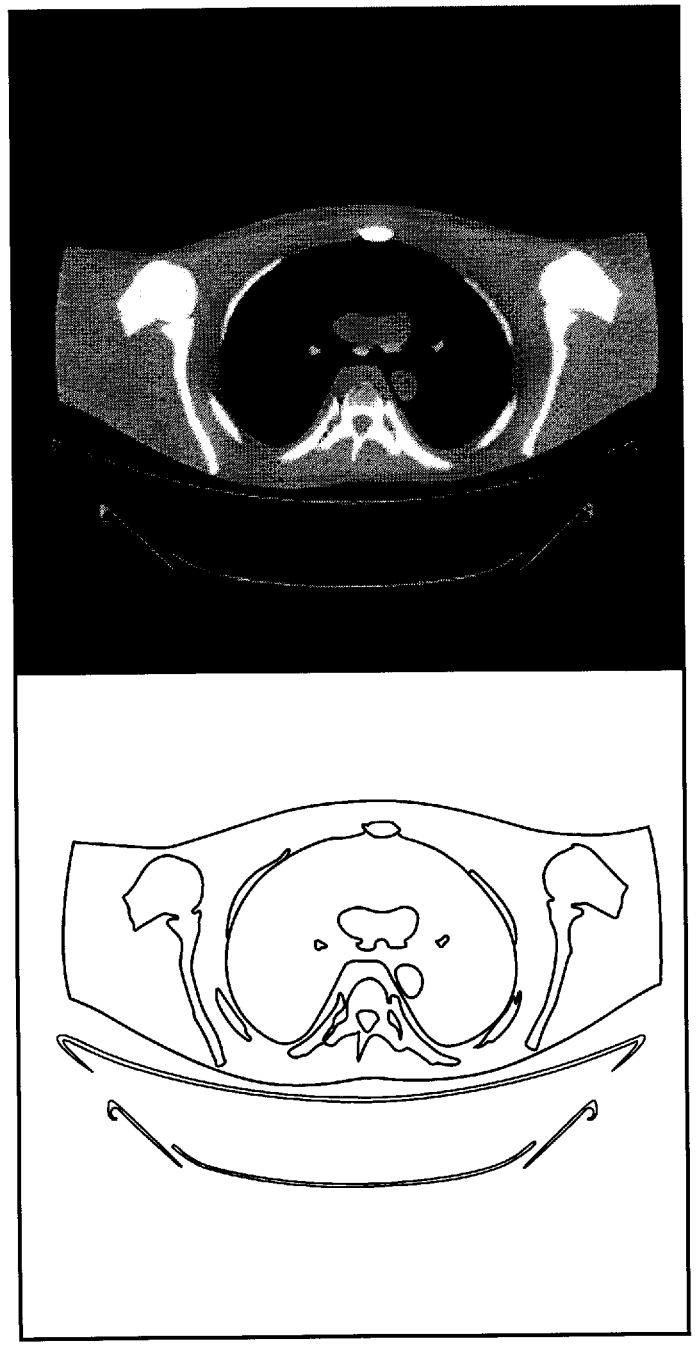
F I G. 5D

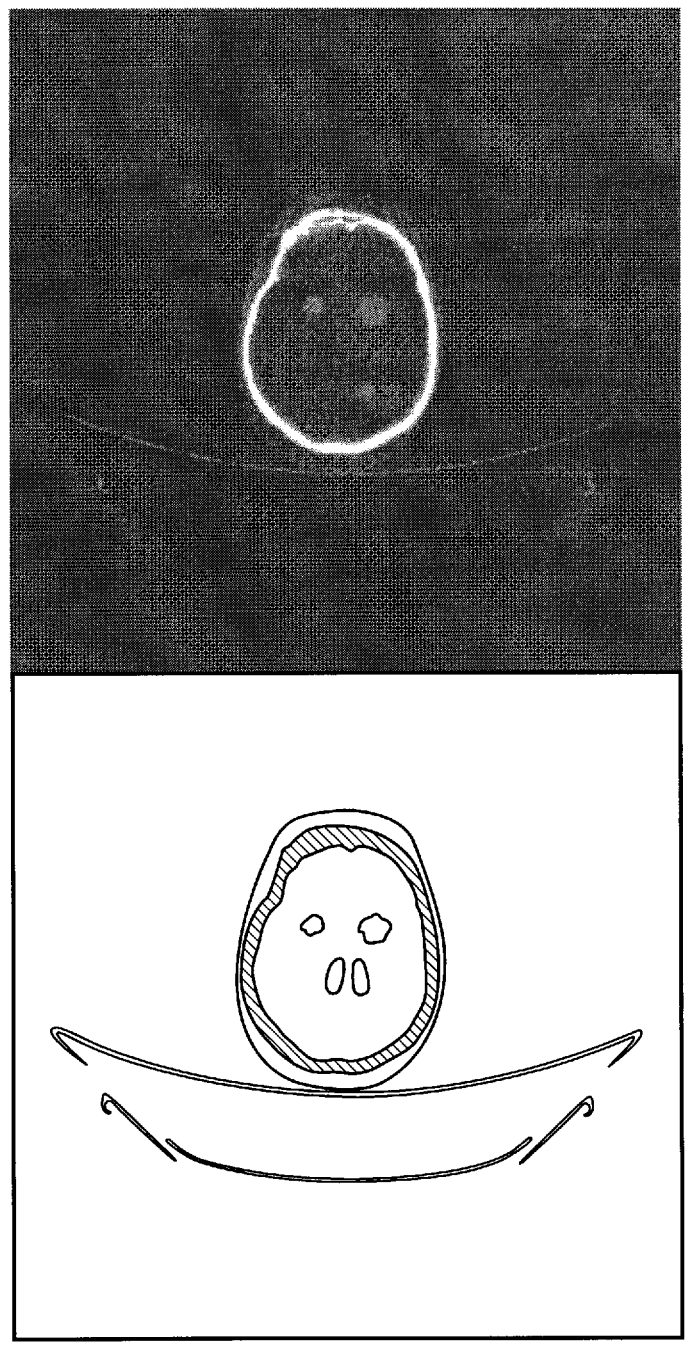
F I G. 6A

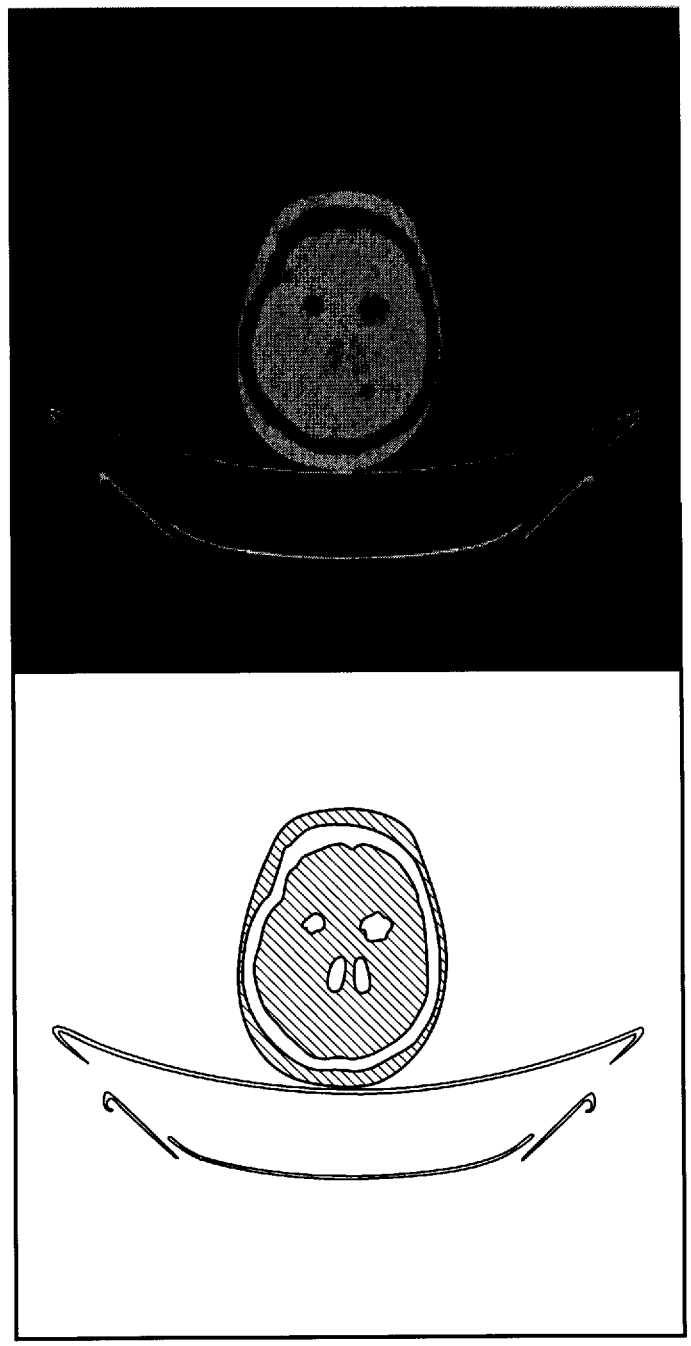
F I G. 6B

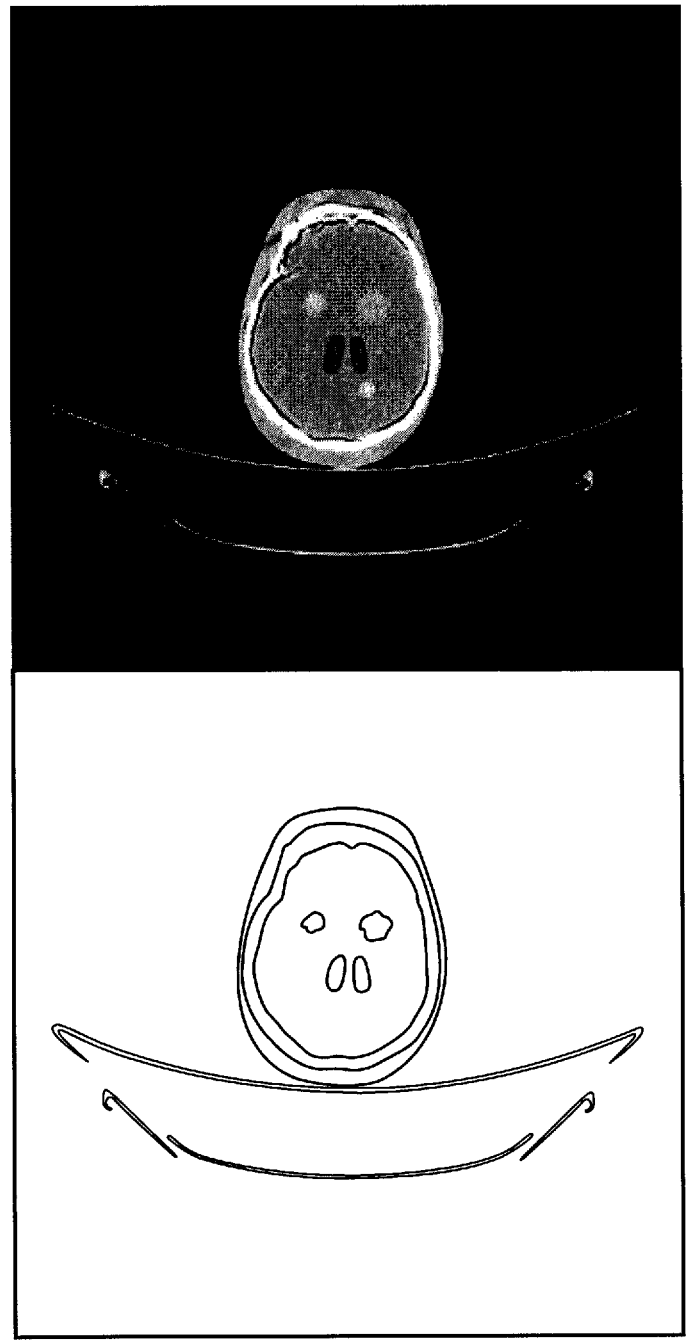
F I G. 6C

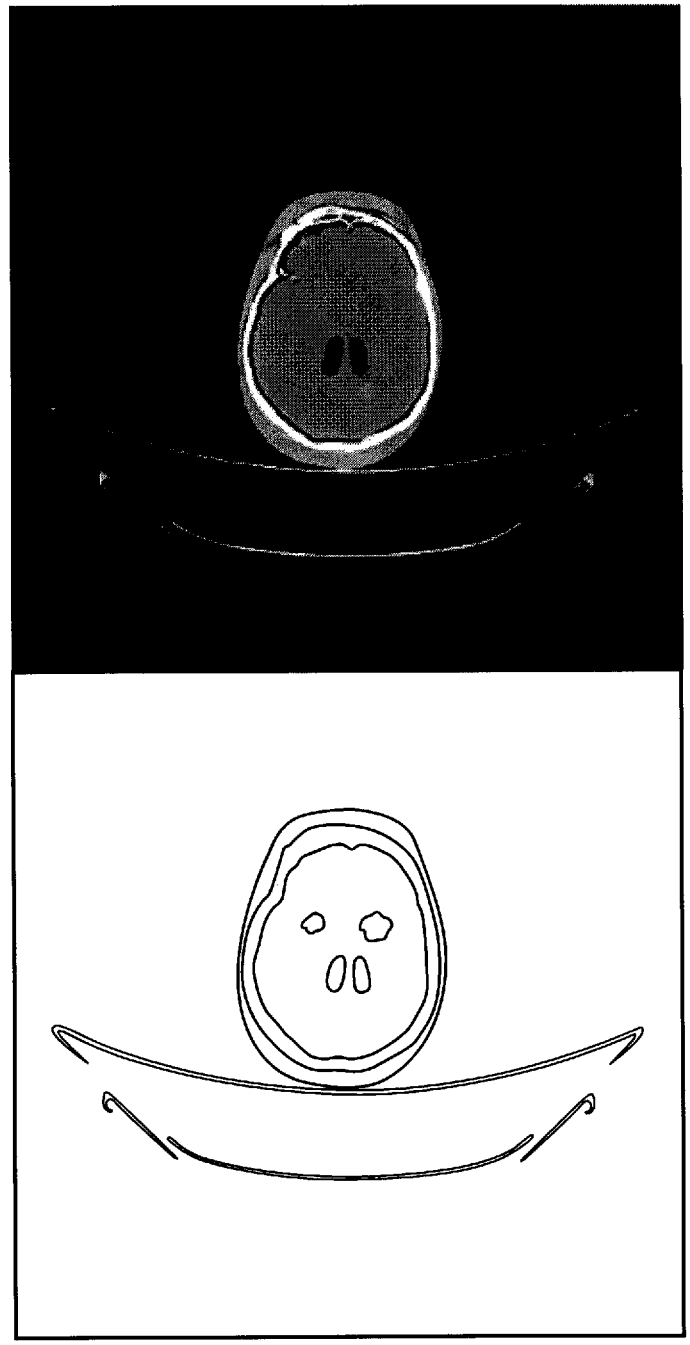
F I G. 6D

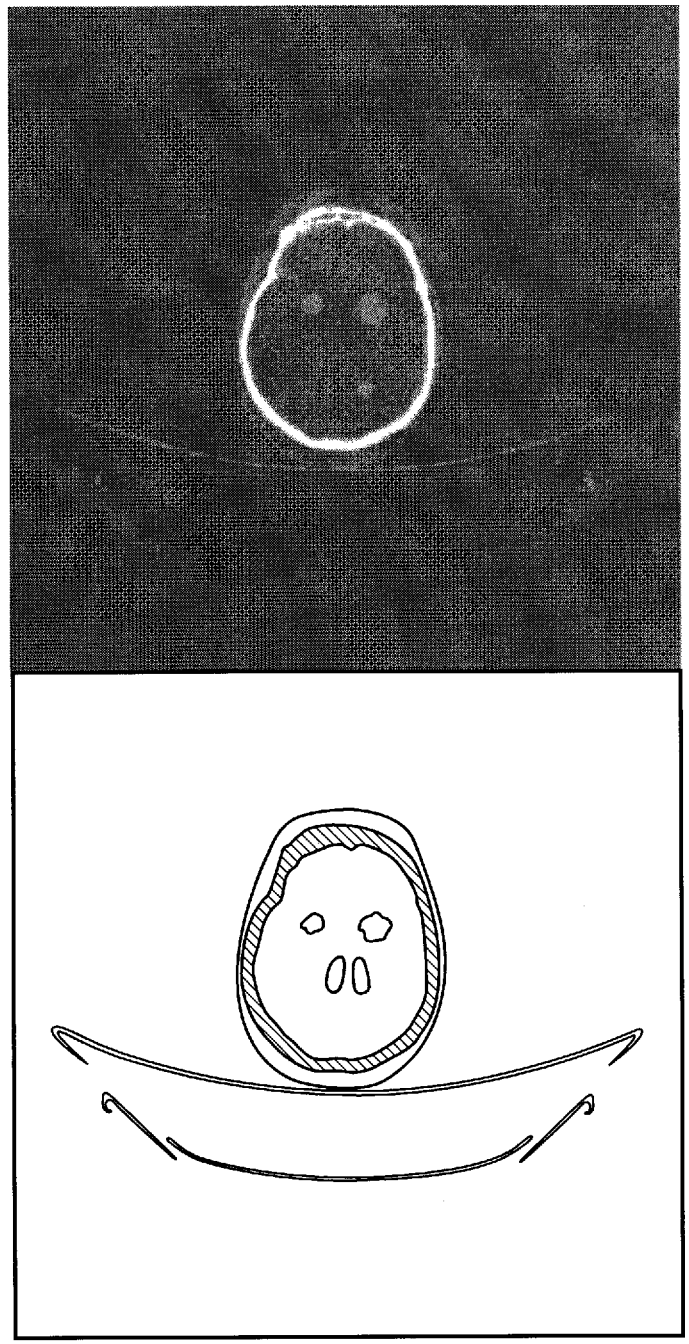
F I G. 7A

WATER

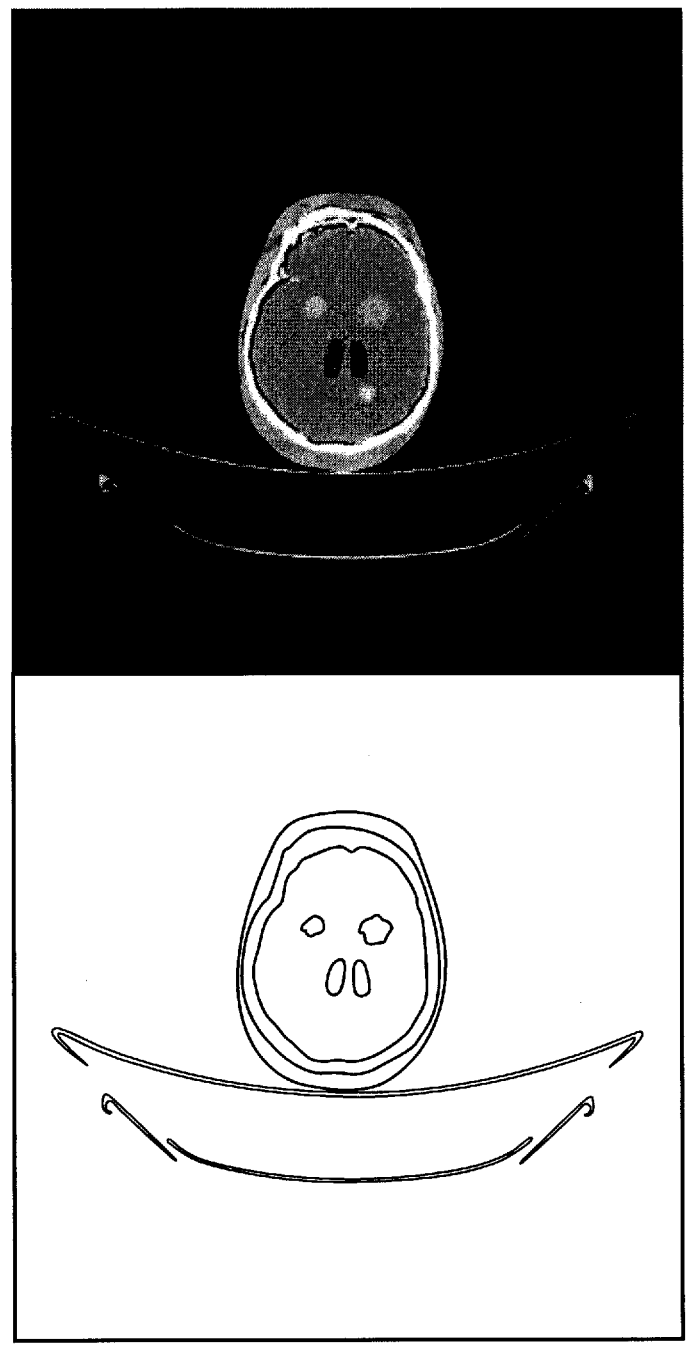
F I G. 7C

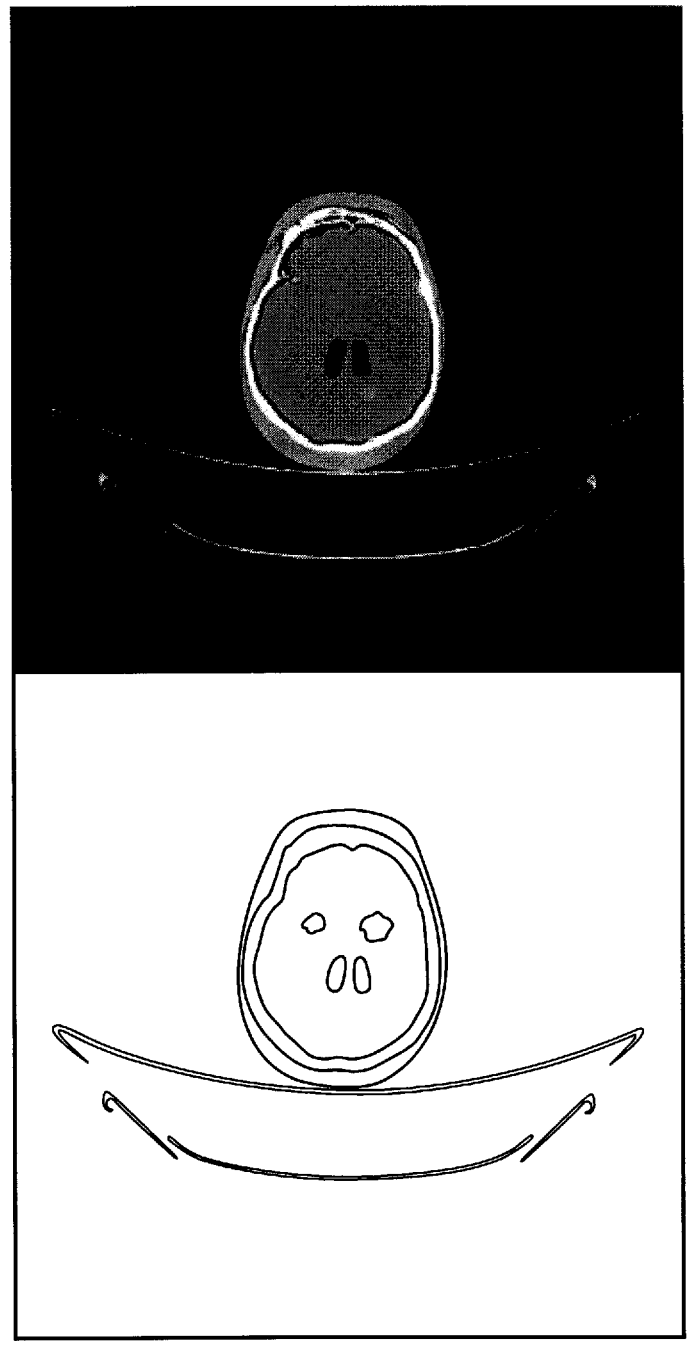
F I G. 7D

X RAY COMPUTER TOMOGRAPHY APPARATUS AND IMAGE PROCESSING APPARATUS

CROSS-REFERENCE TO RELATED APPLICATIONS

This application is based upon and claims the benefit of priority from the prior U.S. patent application Ser. No. 14/137,254 filed Dec. 20, 2013 and Japanese Patent Application No. 2014-235997 filed Nov. 20, 2014 the entire contents of which are incorporated herein by reference.

FIELD

Embodiments described herein relate generally to an X-ray computer tomography apparatus and an image processing apparatus, and more particularly related to iterative reconstruction of CT images based upon the combined data of full views with regard to intensity data and sparse views with regard to spectral data.

BACKGROUND

The x-ray beam in most computer tomography (CT) scanners is generally polychromatic. Yet, most of the currently utilized CT scanners generate images based upon data according to the energy integration nature of the detectors. These conventional detectors are called energy integrating detectors for acquiring energy integration X-ray data that cannot provide spectral information. On the other hand, photon counting detectors are configured to acquire the spectral nature of the x-ray source rather than the energy integration nature in the acquired data. To obtain the spectral nature of the transmitted X-ray, the photo counting detector splits the x-ray beam into its component energies or spectrum bins and counts a number of photons in each of the bins. The use of the spectral nature of the x-ray source in CT is often referred to as spectral CT. Since spectral CT involves the detection of transmitted X-ray at two or more energy levels, spectral CT generally includes dual-energy CT by definition.

Spectral CT is advantageous over conventional CT in certain aspects. Spectral CT offers the additional clinical information inherent in the full spectrum of an x-ray beam. For example, spectral CT enhances in discriminating tissues, differentiating between materials such as tissues containing calcium and iodine or enhancing the detection of smaller vessels. Among other advantages, spectral CT is also expected to reduce beam hardening artifacts. Spectral CT is expected to increase accuracy in CT numbers independent of scanners.

Prior art attempts for spectral CT unfortunately involve tradeoffs while trying to solve issues such as beam hardening, temporal resolution, noise balance, and inadequate energy separation. For example, dual source solutions are good for noise balance and energy separation but are not so good in some clinical applications for correcting beam hardening and improving temporal resolution. Fast kV-switching has the potential for good beam hardening correction and good temporal resolution although the noise balance might require a tradeoff with temporal resolution and inadequate energy separation might affect the precision of the reconstructed spectral images. Nonetheless, when utilized in the right clinical situations, prior art solutions can successfully improve diagnosis. On the other hand, spectral imaging with photon counting detectors has the potential for solving all four issues without tradeoffs as well as more advanced spectral techniques such as precise material characterization through k-edge imaging.

Prior art has also attempted to replace the conventional integrating detectors by the photon counting detectors in implementing spectral CT. In general, photon counting detectors are costly and have performance constraints under high flux x-rays. Although at least one experimental spectral CT system has been reported, the costs of high-rate photon counting detectors are prohibitive for a full-scale implementation. Despite some advancement in the photon counting detector technology, the currently available photon counting detectors still require solutions to implementation issues such as polarization due to space charge build-up, pile-up effects, scatter effects, spatial resolution, temporal resolution and dose efficiency.

Spectral CT is currently limited to dual energy approaches such as dual source CT, dual layer detector CT and fast-kV switching CT. In this regard, true spectral information beyond dual energy is not advantageously utilized in general purpose clinical CT. On the other hand, a true spectral CT system appears to face the above described issues related to the energy differentiating photon counting detectors.

For the above reasons, it is still desired to invent CT systems and methods of improving the use of spectral data as acquired by the photon counting detectors possibly in combination with energy integrated data as acquired by the energy integrating detectors.

BRIEF DESCRIPTION. OF THE DRAWING

FIG. 2A is a view showing an X-ray computer tomography apparatus including an energy integrating detector and photon counting detector both in a third-generation geometry according to the embodiment;

FIG. 2B is a view showing an X-ray computer tomography apparatus including an energy integrating detector in a third-generation geometry and a photon counting detector in a fourth-generation geometry according to the embodiment;

FIG. 4A is a view showing a basis image of bones in a torso phantom based upon intensity data of 140 kVP and 1200 views (full views) and spectral data of 100 kVP and 75 views (sparse views) according to an example based upon a simulation;

FIG. 4B is a view showing a basis image of water in the torso phantom based upon intensity data of 140 kVP and 1200 views (full views) and spectral data of 100 kVP and 75 views (sparse views) according to an example based upon a simulation;

FIG. 4C is a view showing a monochromatic image of the torso phantom in FIGS. 4A and 4B at 50 keV according to an example based upon a simulation;

FIG. 5A is a view showing a basis image of bones in the torso phantom based upon intensity data of 140 kVP and 1200 views (full views) and spectral data of 100 kVP and 150 views (sparse views) according to an example based upon a simulation;

FIG. 5B is a view showing a basis image of water in the torso phantom based upon intensity data of 140 kVP and 1200 views (full views) and spectral data of 100 kVP and 150 views (sparse views) according to an example based upon a simulation;

FIG. 5C is a view showing a monochromatic image of the torso phantom in FIGS. 5A and 5B at 50 keV according to an example based upon a simulation;

FIG. 5D is a view showing a monochromatic image of the torso phantom in FIGS. 5A and 5B at 75 keV according to an example based upon a simulation;

FIG. 6A is a view showing a basis image of bones in a head phantom based upon intensity data of 140 kVP and 1200 views (full views) and sparse spectral data of 100 kVP and 75 views (sparse views) according to an example based upon a simulation;

FIG. 6B is a view showing a basis image of water in the head phantom based upon intensity data of 140 kVP and 1200 views (full views) and spectral data of 100 kVP and 75 views (sparse views) according to an example based upon a simulation;

FIG. 6C is a view showing a monochromatic image of the head phantom in FIGS. 6A and 6B at 50 keV according to an example based upon a simulation;

FIG. 6D is a view showing a monochromatic image of the head phantom in FIGS. 6A and 6B at 75 keV according to an example based upon a simulation;

FIG. 7A is a view showing a basis image of bones in a head phantom based upon intensity data of 140 kVP and 1200 views (full views) and spectral data of 100 kVP and 150 views (sparse views) according to an example based upon a simulation;

FIG. 7C is a view showing a monochromatic image of the head phantom in FIGS. 7A and 7B at 50 keV according to an example based upon a simulation; and FIG. 7D is a view showing a monochromatic image of the head phantom in FIGS. 7A and 7B at 75 keV according to an example based upon a simulation.

DETAILED DESCRIPTION

In general, according to one embodiment, an X-ray computer tomography apparatus includes at least one X-ray tube generating X-rays, first detector elements of an energy integrating type, detecting an intensity of X-rays generated from the X-ray tube and transmitted through an object, second detector elements of a photon counting type detecting a spectrum of X-rays generated from the X-ray tube and transmitted through the object, at least one data acquisition circuit acquiring first projection data detected by the first detector elements and second projection data which is detected by the second detector elements and is smaller in data amount than the first projection data, an arithmetic circuit computing a minimum value of a predetermined cost function based upon the first projection data and the second projection data by executing an iterative reconstruction algorithm, and a reconstruction circuit reconstructing an image of the object based upon the first projection data and the second projection data, which correspond to the minimum value of the cost function.

Figure 1:
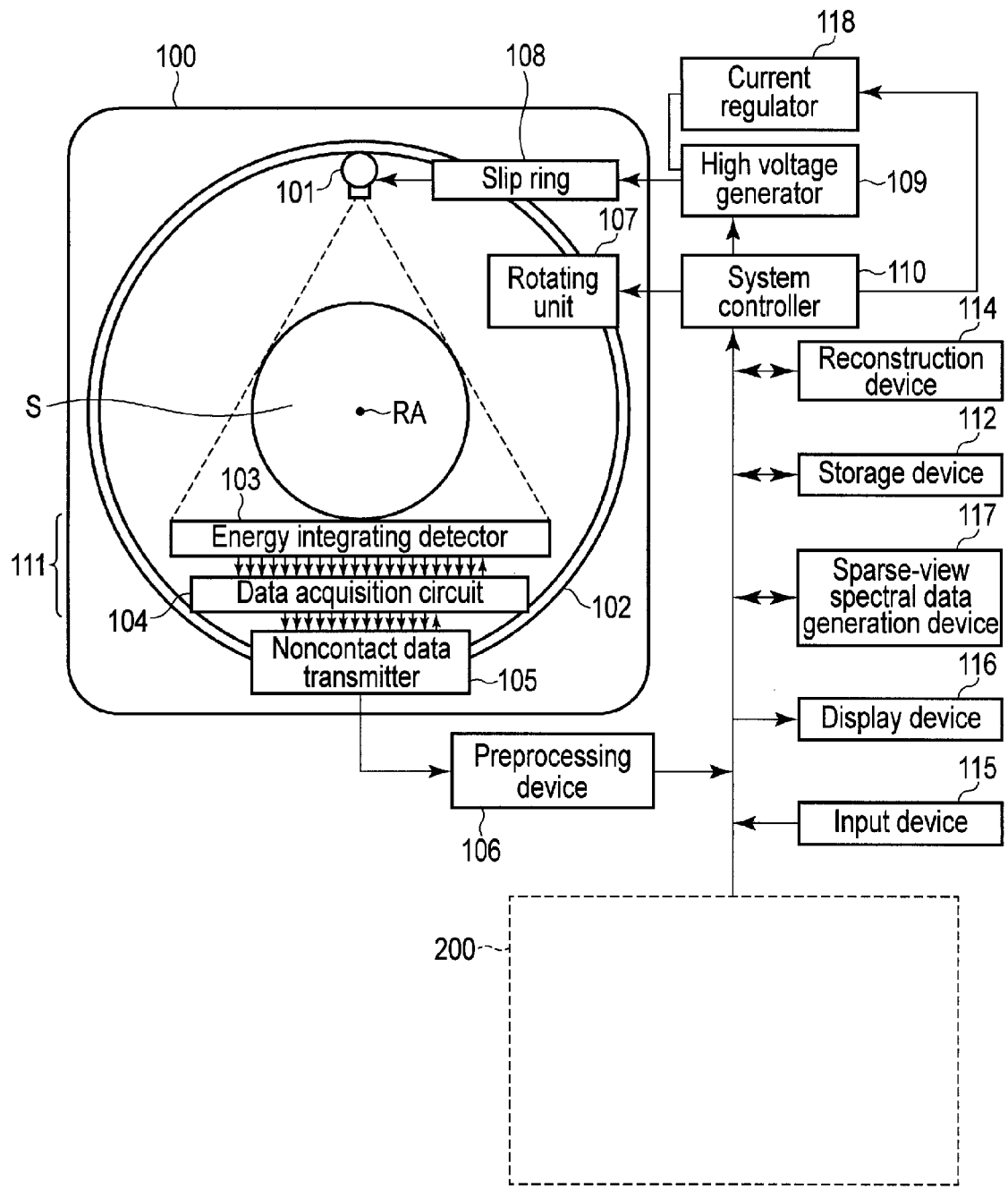
FIG. 1 is a block diagram showing an X-ray computer tomography apparatus including a gantry and other devices and units according to an embodiment.
Figure 3:
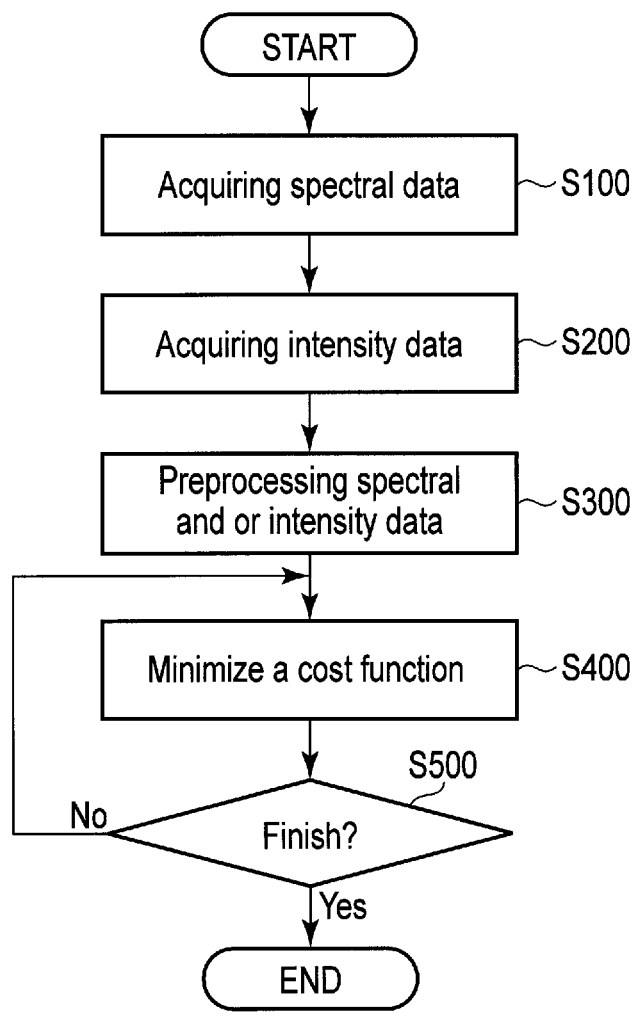
FIG. 3 is a flowchart showing steps or acts associated with a process of reconstructing an image based upon the full views with regard to intensity data and sparse views with regard to spectral data according to the embodiment.

Referring now to the drawings, wherein like reference numerals designate corresponding structures throughout the views, and referring in particular to FIG. 1, a diagram illustrates one X-ray CT apparatus or scanner according to the current invention including a gantry 100 and other devices or units. The gantry 100 is illustrated from a side view and further includes an X-ray tube 101, an annular frame 102 and a multi-row or two-dimensional array type energy integrating detector 103. The X-ray tube 101 and energy integrating detector 103 are diametrically mounted across a subject S on the annular frame 102, which is rotatably supported around a rotation axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 which generates a tube voltage to be applied to an X-ray tube 101 via a slip ring 108 and a current regulator 118 which outputs a constant current to the high voltage generator 109. As a result, the X-ray tube 101 generates X-rays. The X-rays are emitted toward the subject S whose cross sectional area is represented by a circle. The energy integrating detector 103 (first detector) is arranged on the opposite side of the subject S to the X-ray tube 101 to detect emitted X-rays transmitted through the subject S. The energy integrating detector 103 further includes individual first detector elements or units of an energy integrating type.

Still referring to FIG. 1, the X-ray CT apparatus or scanner further includes other devices for processing the detected signals from Energy integrating detector 103. A data acquisition circuit or a Data Acquisition System 104 (DAS) converts a signal output from the Energy integrating detector 103 for each channel into a voltage signal, amplifies it, and further converts it into a digital signal. The Energy integrating detector 103 and the Data Acquisition System 104 are configured to handle a predetermined total number of projections per rotation (TPPR) that can be at the most 900 TPPR, between 900 TPPR and 1800 TPPR and between 900 TPPR and 3600 TPPR.

The above described data is sent to a preprocessing device 106, which is housed in a console outside the gantry 100 through a non-contact data transmitter 105. The preprocessing device 106 performs certain corrections such as sensitivity correction on the raw data. A storage device 112 (memory circuit) then stores the resultant data that is also called projection data at a stage immediately before reconstruction processing. The storage device 112 is connected to a system controller 110 through a data/control bus, together with a reconstruction device 114, an input device 115, a display device 116 and a scan plan support apparatus 200. The scan plan support apparatus 200 includes a function for supporting an imaging technician to develop a scan plan.

The detectors are either rotated or fixed with respect to the patient among various generations of the CT scanner systems. The above described CT system has one exemplary third-generation geometry in which the X-ray tube 101 and the energy integrating detector 103 are diametrically mounted on the annular frame 102 and are moved around the subject S as the annular frame 102 is rotated about the rotation axis RA.

An embodiment of the present invention is configured to acquire the full views with regard to intensity data (first projection data) of the object or the subject S by using the energy integrating detector 103 in a third-generation geometry, and the radiation source or the X-ray tube 101.

FIG. 1 illustrates the use of the rotating energy integrating detector 103 in acquiring projection data in a third-generation geometry for reconstructing an image of the object based upon the full views with regard to intensity data and the sparse views with regard to spectral data. One embodiment initially obtains two data sets of the full views with regard to intensity data respectively with a high energy level such as 135 kV and a low energy level such as 80 kV on a third-generation scanner.

In addition, as will be described later, the sparse views with regard to spectral data of the object (the second projection data: data smaller in data amount than the first projection data) are acquired by using a photon counting detector (second detector) in a third-generation geometry or fourth-generation geometry which is capable of energy discrimination. An image of the object is reconstructed based upon the full views with regard to intensity data and the sparse views with regard to spectral data.

A sparse-view spectral data generation device 117 generates the spectral data (second projection data) of the object or the subject S based upon the sparse views acquired by the photon counting detector (first function).

Note that the sparse-view spectral data generation device 117 further has a function (second function) of generating data based upon sparse views by selecting one view for every N views (e.g., N=8) as a predetermined number in low energy data and discarding the remainders. With the use of this function, the sparse-view spectral data generation device 117 can generate the sparse pairs of low/high energy data, obtained by the energy integrating detector 103, which mimic the spectral data from the sparsely arranged photon counting detector elements. This function is utilized in an example for a simulation to validate the effect of an iterative reconstruction algorithm according to an embodiment of the present invention. The reconstruction device 114 utilizes the full high energy data from a third-generation scanner and the generated sparse spectral data in reconstructing an image.

The energy integrating detector 103 and the photon counting detector need not always be located on the same scanner, and the full views with regard to intensity data and sparse views with regard to spectral data may be simultaneously acquired from a single scanner so as to obtain their spatial and temporal resolutions.

FIG. 2A is a view showing an X-ray computer tomography apparatus including the energy integrating detector 103 and photon counting detector both in a third-generation geometry according to an embodiment. The X-ray computer tomography apparatus has an exemplary third-generation geometry in which the X-ray tube 101 and the energy integrating detector 103 are mounted on the predetermined annular frame 102 so as to face each other, and the annular frame 102 moves the X-ray tube 101 and the energy integrating detector 103 around the subject S while rotating them around a predetermined rotation axis. During the rotation, the X-ray tube 101 moves along a predetermined trajectory while being held at an opposite position facing the energy integrating detector 103. The energy integrating detector 103 detects transmitted X-rays and generates an energy integration signal in full views while the X-ray tube 101 emits X-rays at a predetermined energy level. The intensity data acquiring device acquires full views with regard to intensity data of the subject S or the object as the X-ray tube 101 and the energy integrating detector 103 move around the subject.

Although not shown, the respective detector elements of the photon counting detector are fixedly arranged along the annular frame 102 and the object. In this arrangement, for example, the respective detector elements (second detector element) of the photon counting detector are sparsely arranged as compared with the respective detector elements of the energy integrating detector 103, and generate the second projection data based upon sparse views by detecting transmitted X-rays from the subject while rotating around the subject S. That is, the pitch of the respective detector elements of the photon counting detector is larger than that of the respective detector elements constituting the energy integrating detector 103.

Note that in an example for a simulation, the detector elements of the photon counting detector can acquire full views by being arranged in a row, and then, the second projection data based upon sparse views can also be generated by thinning out the full views by using the second function of the sparse-view spectral data generation device 117.

FIG. 2B is a view showing an X-ray computer tomography apparatus including an energy integrating detector in a third-generation geometry and a photon counting detector in a fourth-generation geometry according to an embodiment. As shown in FIG. 2B, the respective detector elements (PCD1 to PCDN) of the photon counting detector are sparsely mounted inside or along a predetermined path located inside the first trajectory of the energy integrating detector 103 or the second trajectory of the radiation source or X-ray tube 101. In the embodiment shown in FIG. 2B, the trajectory of the X-ray tube 101 has a larger diameter such that a predetermined portion of a predetermined path is encompassed by a predetermined beam angle. In another embodiment, the trajectory of the X-ray tube 101 may have a certain diameter such that a smaller portion of a predetermined path is encompassed by a predetermined beam angle.

In the above relative spatial relationship, the X-ray tube 101 moves along a predetermined path outside the first path of the fixedly arranged photon counting detector while continuously emitting X-rays toward the object. In this regard, the X-ray tube 101 emits X-rays toward the subject S, and some radiation reaches the energy integrating detector 103 after transmitting through the subject S, while other radiation also reaches a certain portion of the photon counting detector, each having a detection surface which is located at a certain angle with respect to the X-ray tube 101. Spectral data is detected by photon counting detectors sparsely fixed with respect to the X-ray tube 101. Energy integration data is detected by the energy integrating detector 103, which rotates together with the X-ray tube 101. Therefore, both the energy integrating detector 103 and the photon counting detector continuously acquire a combination of the data for later reconstruction of an image by the reconstruction device 114. In any case, FIG. 2B shows a combined use of the rotating energy integrating detector 103 and the photon counting detector for acquiring the full views with regard to intensity data and the sparse views with regard to spectral data, respectively.

(Modification)

A modification includes the rotating energy integrating detector 103 and photon counting detector in separate scanners or the housing of a single scanner. That is, the full views with regard to intensity data and sparse views with regard to spectral data are acquired sequentially or independently, but not simultaneously. Although this alternative embodiment may be optionally implemented by sequential or independent scans, the acquired data may have temporal and/or spatial correction before reconstructing an image.

As will be further illustrated, the above described embodiment is a mere example and is not limited in many aspects. For example, although a certain spatial relationship of the trajectories or paths are disclosed among the source or X-ray tube 101, the energy differentiating detectors PCDs and the energy integrating detector 103, the spatial relationship is relative and not limited to a particular relation as illustrated in the diagram. Lastly, although a single pair of the energy integrating detector 103 and the radiation source or X-ray tube 101 is illustrated in the embodiment, an additional pair of the energy integrating detector 103 and the radiation source or X-ray tube 101 is incorporated in another embodiment according to the current invention.

A process of reconstructing an image based upon the full views with regard to intensity data and sparse views with regard to spectral data (iterative reconstruction algorithm) will be described next.

Note that the reconstruction process utilizes both the full views with regard to intensity data and sparse views with regard to spectral data, but is irrelevant to how to acquire intensity data and spectral data before image reconstruction.

The following description is based upon the assumption that the full views with regard to intensity data and sparse views with regard to spectral data are simultaneously acquired by using a single scanner. Note that the full views with regard to intensity data and sparse views with regard to spectral data may be sequentially or independently acquired by using a plurality of scanners.

In step S100, sparse views with regard to spectral data are acquired or obtained and are set in an available state. In step S200, the full views with regard to intensity data are acquired or obtained and are set in an available state. Note that the execution order of steps S100 and S200 may be interchanged or they may be simultaneously executed.

In step S300, the intensity data and/or the spectral data in an available state are optionally preprocessed to form a predetermined cost function. In general, the cost function includes system matrices respectively associated with third-generation and fourth-generation scanners, basis images, intensity data, spectral data, a normalization term (so-called offset adjustment or regularization), and beam hardening correction. Note that in this case, the normalization is optionally turned off or excluded. In addition, the system matrix for third-generation and fourth-generation scanners is expressed by a polar coordinate form. Each cost function to be described below is based upon the total of the sum of square errors between the intensity data in an available state and corresponding true values (first true values) and the sum of square errors between the spectral data in an available state and corresponding true values (second true value).

First of all, an example of the first cost function is provided by equations (1), (2), and (3). Note that each of cost functions including those described later is based upon the total of the sum of square errors between intensity data in an available state and corresponding true values and the sum of square errors between spectral data in an available state and corresponding true values.

$$\psi(c) = \sum_{jn} \frac{1}{\sigma_{jn}^2} (l_n(j) - l_n^{(M)}(j))^2 + \quad (1)$$

$$\sum_j \frac{1}{\sigma_j^2} \left( \sum_{n=1}^N L_n(j)\bar{\mu}_{nM} - g_M(j) - g_M^{(BH)}(L) \right)^2 + wV(c)$$

wherein $$l_n(j) = \sum_i a_{ji} c_n(i) \quad (2)$$

$$L_n(j) = \sum_i A_{ji} c_n(i) \quad (3)$$

where c is a basis image vector, $\sigma_j^2$ is a variance of $l_n^{(M)}(j)$, $\sigma_j^2$ is a variance of $g_M(j)$, $\bar{\mu}_{nM}$ is an average linear attenuation coefficient over a spectrum for a basis n, $a_{ji}$ is a system matrix for a fourth-generation scanner for acquiring the spectral data according to sparse views, $A_{ji}$ is a system matrix for a third-generation matrix for acquiring the intensity data according to full views, $c_n(i)$ is material basis images, V(c) is a normalization term, $g_M(j)$ is the intensity data according to full views, $g_M^{(BH)}(L)$ is a beam-hardening correction term with L being a material length vector of the basis material, $l_n^{(M)}(j)$ is a material length for basis n along a beam j from the spectral data according to sparse views after decomposition, $l_n(j)$ is a re-projected material length for the fourth-generation geometry, and $L_n(j)$ is a re-projected material length for a third-generation geometry. Assume that in this case, a weight w for the normalization term is set to zero (w=0) for turning off the normalization term (offset term).

An example of the second cost function is provided by equations (4), (5), and (6). This cost function requires no data decomposition for spectral data.

wherein $$\psi(c) = \sum_{jm} \frac{1}{\sigma_{jm}^2} \left( g_m(j) - \sum_{n=1}^N l_n(j)\bar{\mu}_{nm} + g_M^{(BH)}(l) \right)^2 + \quad (4)$$

$$\sum_j \frac{1}{\sigma_j^2} \left( \sum_{n=1}^N L_n(j)\bar{\mu}_{nM} - g_M(j) - g_M^{(BH)}(L) \right)^2 + w(c)V(c)$$

$$l_n(j) = \sum_i a_{ji} c_n(i) \quad (5)$$

$$L_n(j) = \sum_i A_{ji} c_n(i) \quad (6)$$

where c is a basis image vector, $\sigma_{jm}^2$ is a variance of $g_m(j)$, $\sigma_j^2$ is a variance of $g_M(j)$, $\bar{\mu}_{nM}$ is an average linear attenuation coefficient over a spectrum for a basis n, $a_{ji}$ is a system matrix for a fourth-generation scanner for acquiring spectral data according to sparse views, $A_{ji}$ is a system matrix for a third-generation scanner for acquiring the intensity data according to full views, $c_n(i)$ is material basis images, V(c) is a normalization term, $g_m(j)$ is projection data or spectral data for an energy bin m along the beam j, $g_M(j)$ is intensity data, $g_M^{(BH)}(L)$ is a beam-hardening correction term with L being a material length vector of the basis material, $l_n(j)$ is a re-projected material length for spectral data, and $L_n(j)$ is a re-projected material length for intensity data. Assume that in this case, a weight w or w(c) for the normalization term is set to zero (w=0 or w(c)=0) for turning off the normalization term.

An example of the third cost function is provided by equations (7), (8), and (9). The cost function (7) needs pre-decomposition of spectral data and weighting by a predetermined information matrix such as a Fisher information matrix.

$$\psi(c) = \sum_{jnn'} I_{nn'}(j) \left( \sum_i a_{ji} c_n(i) - l_n^{(M)}(j) \right) \left( \sum_{i'} a_{ji'} c_{n'}(i') - l_{n'}^{(M)}(j) \right) + \quad (7)$$

$$\sum_j \frac{1}{\sigma_j^2} \left( \sum_{n=1}^N L_n(j)\bar{\mu}_{nM} - g_M(j) - g_M^{(BH)}(L) \right)^2 + wV(c)$$

wherein $$l_n(j) = \sum_i a_{ji} c_n(i) \quad (8)$$

$$L_n(j) = \sum_i A_{ji} c_n(i) \qquad (9)$$

Fisher information matrix is defined by the following terms:

$$I_{nn'}(j) = \sum_E \frac{1 \partial N_j(E) \partial N_j(E)}{N_j(E) \partial l_n(j) \partial l_{n'}(j)}$$

where $N_j(E)$ is a photon count (count number) in an energy bin E for a beam path j, c is a basis image vector, $\sigma_j^2$ is variance of $g_M(j)$, $\bar{\mu}_{nM}$ is an average linear attenuation coefficient over a spectrum for a basis n, $a_{ij}$ is a system matrix for a fourth-generation scanner for acquiring spectral data according to sparse views, $A_{ij}$ is a system matrix for a third-generation scanner for acquiring the intensity data according to full views, $c_n(i)$ is a material basis image, for a material n at a pixel i, V(c) is a regulation term, $g_M(j)$ is the intensity data according to full views, $g_M^{(BH)}(L)$ is a beam-hardening correction term with L being a material length vector of the basis material, $l_n^{(M)}(j)$ is a material length for a basis n along a beam j from spectral data according to sparse views after decomposition, $l_n^{(M)}(j)$ is a basis line integral in a fourth-generation geometry (after data area decomposition) for the material n and the beam j from measurement, $l_n(j)$ is a re-projected material length for spectral data, and $L_n(j)$ is a re-projected material length for intensity data. Assume that in this case, a weight w for the normalization term is set to zero (w=0) for turning off the normalization term.

An example of the fourth cost function is provided by equation (10). The cost function (10) needs pre-decomposition of both intensity data and spectral data and weighting by a predetermined information matrix such as a Fisher information matrix.

$$\psi(c) = \sum_{jnn'} I_{nn'}(j) \left( \sum_i a_{ji} c_n(i) - l_n^{(M)}(j) \right) \left( \sum_{i'} a_{ji'} c_{n'}(i') - l_{n'}^{(M)}(j) \right) + \sum_{jn} \frac{1}{\sigma_{jn}^2} \left( \sum_i A_{ji} c_n(i) - L_n^{(M)}(j) \right)^2 + wV(c) \qquad (10)$$

Fisher information matrix is defined by the following terms:

$$I_{nn'}(j) = \sum_E \frac{1 \partial N_j(E) \partial N_j(E)}{N_j(E) \partial l_n(j) \partial l_{n'}(j)}$$

where $N_j(E)$ is a photon count in an energy bin E for a beam path j, c is a basis image vector, $\sigma_{jn}^2$ is a variance of $L_n^{(M)}(j)$, $a_{ij}$ is a system matrix for a fourth-generation scanner for acquiring spectral data according to sparse views, $A_{ij}$ is a system matrix for a third-generation scanner for acquiring the intensity data according to full views, $c_n(i)$ or $c_n(i)$ is material basis images, V(c) is a normalization term, $l_n^{(M)}(j)$ is a material length for a basis n along a beam j from spectral data according to sparse views after decomposition, and $L_n^{(M)}(j)$ is a re-projected material length for intensity data from spectral data according to sparse views after decomposition. Assume that in this case, a weight w for the normalization term is set to zero (w=0) for turning off the normalization term. $L_n^{(M)}(j)$ is determined by $$\sum_{n=1}^N L_n^{(M)}(j) \bar{\mu}_{nM} - g_M(j) - g_M^{(BH)}(L) = 0$$

$$\sum_{n=1}^N \left[ L_n^{(M)}(j) - \sum_i A_{ji} c_n(i) \right] \mu_n(E) = 0$$

where $g_M(j)$ is the intensity data according to full views, $g_M^{(BH)}(L)$ is a beam-hardening correction term with L being a material length vector of the basis material, and $\bar{\mu}_n$ is a basis function (usually a linear attenuation coefficient of a material n at energy E).

As described above with reference to step S300, a process of reconstructing an improved image forms a predetermined cost function based upon intensity data and spectral data. Although a penalty or normalization term is optionally included, it is possible to perform weighting like that in the above embodiment. In addition, a process according to the embodiment is not limited to the above exemplified cost functions, and another cost function is optionally utilized when finally reconstructing an improved image based upon spectral data according to sparse views and the intensity data according to full views according to one process of the embodiment. The ratio between the number of spectral data according to sparse views and the number of the intensity data according to full views is not limited to a specific value either and has an appropriate range based upon a plurality of factors such as a clinical application and the like.

Furthermore, the predetermined cost function is minimized to find a spectral image (that is, an image is obtained, which minimizes the cost function. The details of this operation will be described in association with steps S400 and S500.)

In step S400, a predetermined cost function based upon intensity data and spectral data is minimized by using a predetermined iterative procedure (iterative reconstruction algorithm) in one process of improving an image according to the current application. In general the basis image $c_n(i)$ is updated or initialized during the iterative procedure as seen in Equation (11) given below:

$$c_n(i) = c_n^{(0)}(i) - \frac{\frac{\partial \psi(c^{(0)})}{\partial C_n(i)}}{\sum_{i'n'} \frac{\partial^2 \psi(c^{(0)})}{\partial C_n(i) \partial C_{n'}(i')}} \qquad (11)$$

Equation (11) is an exemplary algorithm which is derived according to the cost function as provided by Equation (1) and is not limited to this specific equation. In fact, there are other equations corresponding to the above exemplary cost functions represented by Equations (4), (7), and (10).

The above iterative procedure is repeated in steps S400 and S500 in order to find a spectral image having a positivity constraint in one process of improving an image utilizing intensity data and spectral data according to the embodiment. This iteration is repeated if a predetermined condition (the value of the cost function is equal to or less than a predetermined value) has not yet been met when it is determined in step S500. On the other hand, the iteration is terminated if the predetermined condition is reached when it is determined in the step S500. The predetermined condition for termination is not limited to a specific condition and includes several conditions such as a predetermined maximum iteration count or the difference in a certain value between the current instance and the previous instance. The predetermined terminating condition also optionally depends upon other conditions such as a clinical application.

The image reconstructed from the intensity data obtained from the energy integrating detector 103 in a third-generation geometry contains no spectral information. On the other hand, although the images reconstructed from the spectral data obtained from the photon counting detector in a fourth-generation geometry contains spectral information, the reconstructed image may contain aliasing artifacts due to a small number of sparse views if the spectral data is processed by itself. An example according to the embodiment, therefore, combines two data sets of intensity data and spectral data and processes the combined data by an iterative procedure. In the above third-generation+fourth-generation spectral CT, the spectral data from the sparse photon counting detector provides spectral information while the intensity data from the energy integrating detector 103 provides an energy integrated value. The combined data has improved an image so as to make it have spectral information, and the improved image is substantially free from aliasing artifacts even if the spectral data is acquired from sparse photon counting detector.

(Example for Simulation)

An example for a simulation will be described. This example utilizes the second function of the sparse-view spectral data generation device 117 in FIG. 1.

That is, the sparse-view spectral data generation device 117 generates the sparse pairs of low/high energy data (for example, a pair of 80 kV and 135 kV), which is actually the intensity data obtained from the energy integrating X-ray detector in a third-generation geometry, mimicking the spectral data from the photon counting detector in a fourth-generation geometry.

Figure 4D:
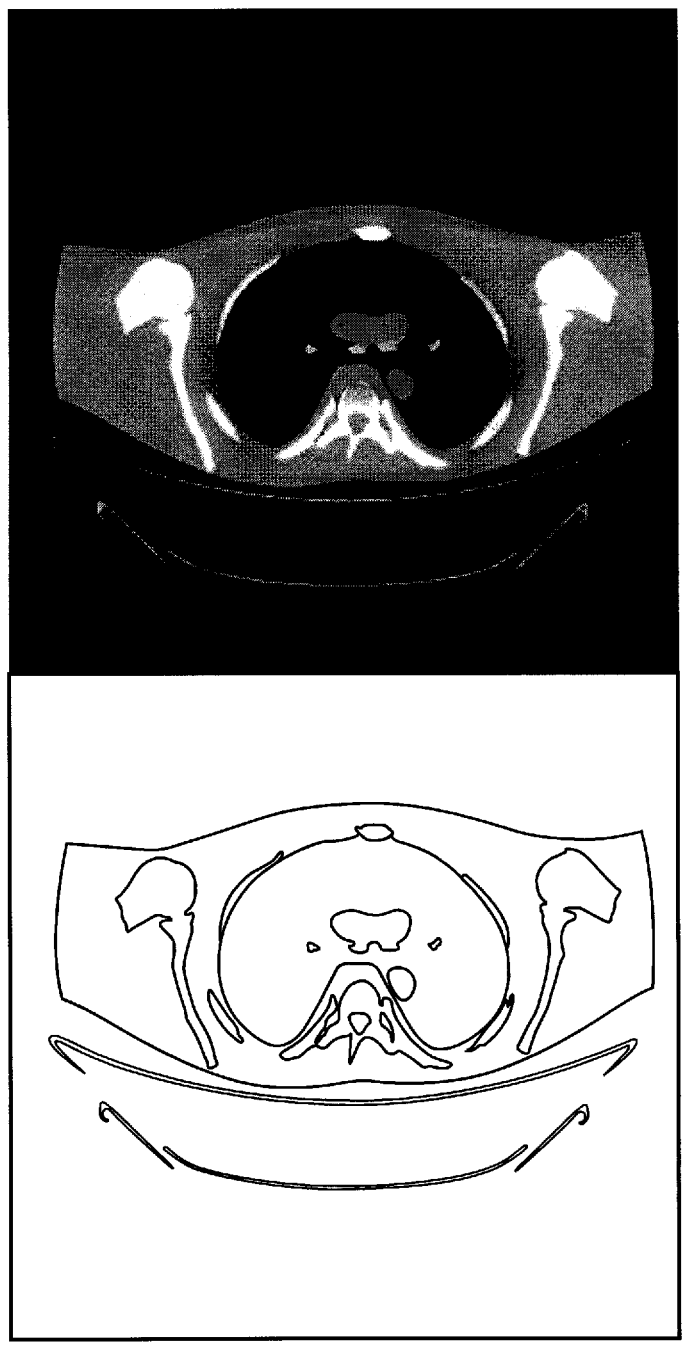
FIG. 4D is a view showing a monochromatic image of the torso phantom in FIGS. 4A and 4B at 75 keV according to an example based upon a simulation.

Now referring to FIGS. 4A through 4D, images illustrate some result of the above described process utilizing the combined data of sparse spectral data and full integration data of a predetermined torso phantom according to the current invention. The full integration data is based upon 140 kVP and 1200 views of the circular scans. The sparse spectral data is based upon 100 kVP and 75 views. FIG. 4A is a basis image for bone while FIG. 4B is a basis image for water. FIG. 4C is a monochromatic image at 50 keV while FIG. 4D is a monochromatic image at 75 keV.

Now referring to FIGS. 5A through 5D, images illustrate some result of the above described process utilizing the combined data of sparse spectral data and full integration data of a predetermined torso phantom according to the current invention. The full integration data is based upon 140 kVP and 1200 views of the circular scans. The sparse spectral data is based upon 100 kVP and 150 views. FIG. 5A is a basis image for bone while FIG. 5B is a basis image for water. FIG. 5C is a monochromatic image at 50 keV while FIG. 5D is a monochromatic image at 75 keV.

Now referring to FIGS. 6A through 6D, images illustrate some result of the above described process utilizing the combined data of sparse spectral data and full integration data of a predetermined head phantom according to the current invention. The full integration data is based upon 140 kVP and 1200 views of the circular scans. The sparse spectral data is based upon 100 kVP and 75 views. FIG. 6A is a basis image for bone while FIG. 6B is a basis image for water. FIG. 6C is a monochromatic image at 50 keV while FIG. 6D is a monochromatic image at 75 keV.

Figure 7B:
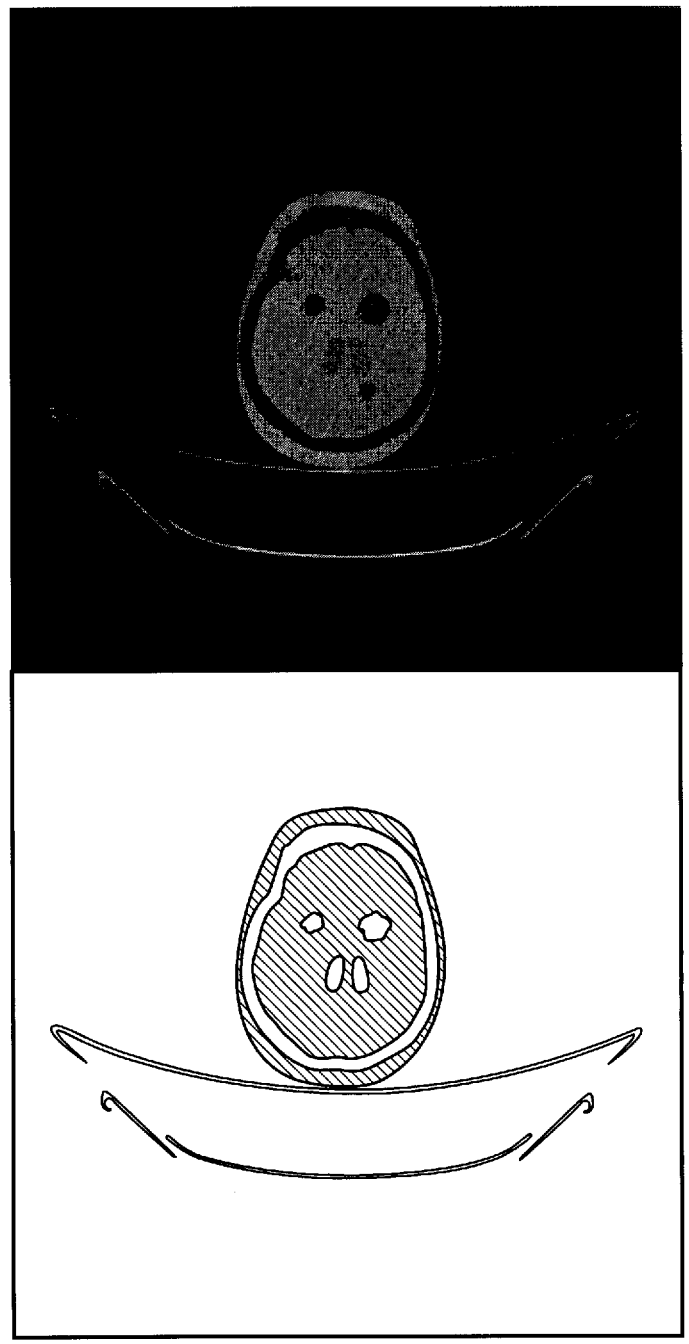
FIG. 7B is a view showing a basis image of water in the head phantom based upon intensity data of 140 kVP and 1200 views (full views) and spectral data of 100 kVP and 150 views (sparse views) according to an example based upon a simulation.

Now referring to FIGS. 7A through 7D, images illustrate some result of the above described process utilizing the combined data of sparse spectral data and full integration data of a predetermined head phantom according to the current invention. The full integration data is based upon 140 kVP and 1200 views of the circular scans. The sparse spectral data is based upon 100 kVP and 150 views. FIG. 7A is a basis image for bone while FIG. 7B is a basis image for water. FIG. 7C is a monochromatic image at 50 keV while FIG. 7D is a monochromatic image at 75 keV.

The embodiment has exemplified the case in which the X-ray computer tomography apparatus executes reconstruction processing to reconstruct an image of an object by the iterative reconstruction algorithm using the full views with regard to intensity data obtained from the energy integrating detector 103 and sparse views with regard to spectral data obtained from the photon counting detector. However, the example is not limited to this, and may be configured to implement this processing by installing a dedicated image processing program for executing the iterative reconstruction algorithm in an image processing apparatus and processing data obtained from a scanner connected to the image processing apparatus by activating the program.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray computer tomography apparatus comprising:
at least one X-ray tube configured to generate X-rays;
a plurality of first detector elements of an energy integrating type, configured to detect an intensity of X-rays generated from the X-ray tube and transmitted through an object;
a plurality of second detector elements of a photon counting type, configured to detect a spectrum of X-rays generated from the X-ray tube and transmitted through the object;
at least one data acquisition circuit configured to acquire first projection data detected by the plurality of first detector elements and second projection data which is detected by the plurality of second detector elements and is smaller in data amount than the first projection data;
an arithmetic circuit configured to compute a minimum value of a predetermined cost function based upon the first projection data and the second projection data by executing an iterative reconstruction algorithm; and
a reconstruction circuit configured to reconstruct an image of the object based upon the first projection data and the second projection data, which correspond to the minimum value of the cost function.

2. The X-ray computer tomography apparatus according to claim 1, wherein the data acquisition circuit is configured to acquire the second projection data smaller in view count than the first projection data.

3. The X-ray computer tomography apparatus according to claim 1, wherein the plurality of second detector elements are detector elements arranged at a pitch larger than a pitch of the plurality of first detector elements.

4. The X-ray computer tomography apparatus according to claim 1, wherein an arrangement of the plurality of first detector elements includes a third-generation geometry.

5. The X-ray computer tomography apparatus according to claim 1, wherein an arrangement of the plurality of second detector elements includes one of a third-generation geometry and a fourth-generation geometry.

6. The X-ray computer tomography apparatus according to claim 1, wherein the cost function is based upon a total of a sum of square errors between the first projection data and first true values and a sum of square errors between the second projection data and second true values.

7. The X-ray computer tomography apparatus according to claim 1, wherein the iterative reconstruction algorithm is configured to minimize the cost function by using at least one of polar coordinates, system matrix, normalization, initialization, updating, positivity constraint, and penalty.

8. The X-ray computer tomography apparatus according to claim 1, wherein the second projection data includes a count number with respect to a predetermined number of energy bins.

9. The X-ray computer tomography apparatus according to claim 1, wherein the data acquisition circuit is configured to simultaneously acquire the first projection data and the second projection data.

10. The X-ray computer tomography apparatus according to claim 1, wherein the data acquisition circuit is configured to sequentially acquire the first projection data and the second projection data.

11. An image processing apparatus comprising:
a memory circuit configured to store first projection data detected by a plurality of first detector elements of an energy integrating type and second projection data which is detected by a plurality of second detector elements of a photon counting type and is smaller in data amount than the first projection data;
an arithmetic circuit configured to compute a minimum value of a predetermined cost function based upon the first projection data and the second projection data by executing an iterative reconstruction algorithm; and
a reconstruction circuit configured to reconstruct an image of an object based upon the first projection data and the second projection data, which correspond to the minimum value of the cost function.

* * * * *